(12) United States Patent
Kumar et al.

(10) Patent No.: US 8,034,293 B2
(45) Date of Patent: Oct. 11, 2011

(54) AUTOMATED DIAGNOSTIC WORKSTATION

(75) Inventors: Vijay Kumar, Williamsville, NY (US);
William J. Maggio, Buffalo, NY (US);
Gregory E. Lowe, Mississauga (CA);
Kishore S. Malyavantham,
Williamsville, NY (US)

(73) Assignee: IMMCO Diagnostics, Inc., Buffalo, NY (US)

( * ) Notice: Subject to any disclaimer, the term of this patent is extended or adjusted under 35 U.S.C. 154(b) by 0 days.

(21) Appl. No.: 12/509,163

(22) Filed: Jul. 24, 2009
(Under 37 CFR 1.47)

(65) Prior Publication Data

US 2011/0071039 A1    Mar. 24, 2011

Related U.S. Application Data

(60) Provisional application No. 61/083,378, filed on Jul. 24, 2008.

(51) Int. Cl.
*G01N 21/00*   (2006.01)

(52) U.S. Cl. .............. 422/65; 422/64; 422/67; 422/500; 422/501; 436/180

(58) Field of Classification Search .............. 422/64–65, 422/67, 500–501; 436/180
See application file for complete search history.

(56) References Cited

U.S. PATENT DOCUMENTS

| | | |
|---|---|---|
| 2002/0092770 A1 | 7/2002 | Hedberg et al. |
| 2002/0182117 A1 | 12/2002 | Coassin et al. |
| 2005/0054083 A1 | 3/2005 | Vuong et al. |
| 2006/0210435 A1 | 9/2006 | Alavie et al. |

*Primary Examiner* — Jyoti Nagpaul
(74) *Attorney, Agent, or Firm* — Hodgson Russ LLP

(57) ABSTRACT

A flexible diagnostic workstation comprises is equipped to read label information on well strips of loaded well plates and on loaded reagent kit holders, automatically perform the pre-analytical steps of an immuno-assay which consists of a sequence of operations in accordance with scheduled test requirements for each microwell, read the results according to either a standard singleplex ELISA or multiplex test format as indicated by the well strip label, and report the results.

21 Claims, 16 Drawing Sheets

AUTOMATED DIAGNOSTIC WORKSTATION

CROSS-REFERENCE TO RELATED APPLICATION

This application claims the benefit of priority to U.S. provisional patent application Ser. No. 61/083,378, filed on Jul. 24, 2008, which application is hereby incorporated by reference.

FIELD OF THE INVENTION

The present invention relates generally to diagnostic workstations for performing immuno-assay analysis of biological samples, and more particularly to an automated diagnostic workstation having the flexibility to simultaneously perform immuno-assay and analysis using either a standard Enzyme-Linked ImmunoSorbent Assay ("ELISA") in a singleplex format, a multiplex immuno-assay in a planar microarray, or bar coded bead array format, as required by a particular reaction well.

BACKGROUND OF THE INVENTION

Enzyme-Linked ImmunoSorbent Assay ("ELISA") is a biochemical technique commonly used as a medical diagnostic tool to detect the presence of an antibody or an antigen in a sample. During an ELISA test, a sample containing an analyte is subjected to a biochemical process taking place within an individual microwell of a multi-well plate (also known as a "microtiter plate"), for example a standard 96-well plate has an 8×12 array of individual microwells. Depending on the particular test being conducted, a predetermined capture antibody or bio-molecule may be immobilized on the bottom surface of each microwell, and controlled amounts of various fluids (e.g. blocking solution, washing solution, test sample, detection antibody, primary and secondary antibodies, and substrate) may be added to the microwell according to a predetermined protocol that may include periods of controlled incubation and washes. The result of the biochemical process may be viewed using an optical detector measuring absorbance, fluorescence, and/or luminescence, or other properties, to provide a qualitative and/or quantitative test result.

In traditional ELISA testing, all of the wells in a standard 96-well plate are tested for the same analyte, and a single ELISA protocol is used for the entire plate. This standard ELISA has been extended into a profile screen for a panel of analytes in special cases where in each 8 well strip of a plate has a specific analyte. Consequently, if it is necessary to test for more than one analyte, traditional ELISA is costly with respect to sample volume, reagents, and total throughput time.

Newer multiplexed immuno-assay formats provide a multiplexed platform (known as a microarray) containing individual spots of different antigens or capture antibodies on a single microwell bottom. Alternatively, a multiplexed immuno-assay may comprise magnetic bar-coded particles on which specific analyte molecules are immobilized whereby samples may be tested simultaneously for multiple analytes. Each particle is uniquely identified by the barcode. As such, a plurality of bar-coded particles may be provided in each microwell.

A variety of prepared well plates and well strips (a linear strip of wells inserted into a well plate) are commercially available in either standard singleplex or multiplex formats, and specific reagent kits are also commercially available for performing different ELISA/immuno-assay protocols.

Heretofore, automated diagnostic workstations have been designed to perform either standard (singleplex) ELISA testing or multiplex immuno-assay testing, but not both. The standard ELISA workstations are widely used in clinical as well as research settings, whereas higher-priced microarray or magnetic bar-coded particle processing and scanning workstations tend to be found mainly in research settings. Because prior art workstations cannot combine a standard singleplex ELISA based on colorimetry/absorbance with multiplex immuno-assay formats, all the microwells in commercially available well plates are configured either for standard singleplex ELISA or multiplex immuno-assays. Both standard and multiplex wells are not found in the same microtiter plate.

Also, information about loaded well plates and reagent kits may need to be manually programmed into such workstations by an operator to permit full automation of the associated protocol, which can lead to human error.

SUMMARY OF THE INVENTION

Therefore, it is an object of the present invention to provide a diagnostic workstation system having flexibility to perform both standard singleplex ELISA and multiplex immuno-assay testing.

It is another object of the present invention to provide a diagnostic workstation and well plate having well strips, enabling both standard singleplex ELISA and multiplex immuno-assay microwells to be processed in a single microtiter plate.

It is a further object of the present invention to reduce error by providing barcoded well strips presenting automatically-readable information about the format and protocol associated with each well strip, and bar-coded reagent kit holders presenting automatically-readable information assignable to the type of reagent kit loaded into the holder.

In order to achieve these objects, a well plate is provided with a plurality of unique machine-readable labels, one for each well strip of the microtiter plate. Each label includes information indicating whether the individual microwells in the strip are configured in standard, microarray, or magnetic bar-coded particle format, and indicating the particular test protocol applicable to each microwell. Reagent kit holders are also provided for receiving the reagent bottles found in standard commercially available reagent kits, each kit holder having a unique machine-readable label which may be assigned or correlated with a scannable UPC code on a reagent kit box such that the label on the holder identifies the type of immuno-assay protocol for which the reagents in the holder are intended and enables the reagent kit holder to be mapped. As a result, the user may be presented with a menu of possible test choices to help the user assemble a scheduled test matrix including both standard single-plex and multiplex (microarray) immuno-assay formats. The machine-readable labels may be barcodes.

A diagnostic workstation of the present invention comprises a controller for controlling operation of the workstation. The workstation is equipped to read the machine-readable information on each well strip and reagent kit holder, perform ELISA sequence operations in accordance with the test requirements for each microwell, and read the results according to the appropriate test format (based on standard colorimetry or multiplexed CCD imaging) for each microwell. The addition of a modified CCD and colorimetry reader and custom software allows the CCD based reading of luminescence for cell based functional assays in addition to fluorescence, chemi-luminiscence and transmitted light imaging involved in multiplex assays.

BRIEF DESCRIPTION OF THE DRAWING FIGURES

The nature and mode of operation of the present invention will now be more fully described in the following detailed description of the invention taken with the accompanying drawing figures, in which.

DETAILED DESCRIPTION OF THE INVENTION

Figure 1:
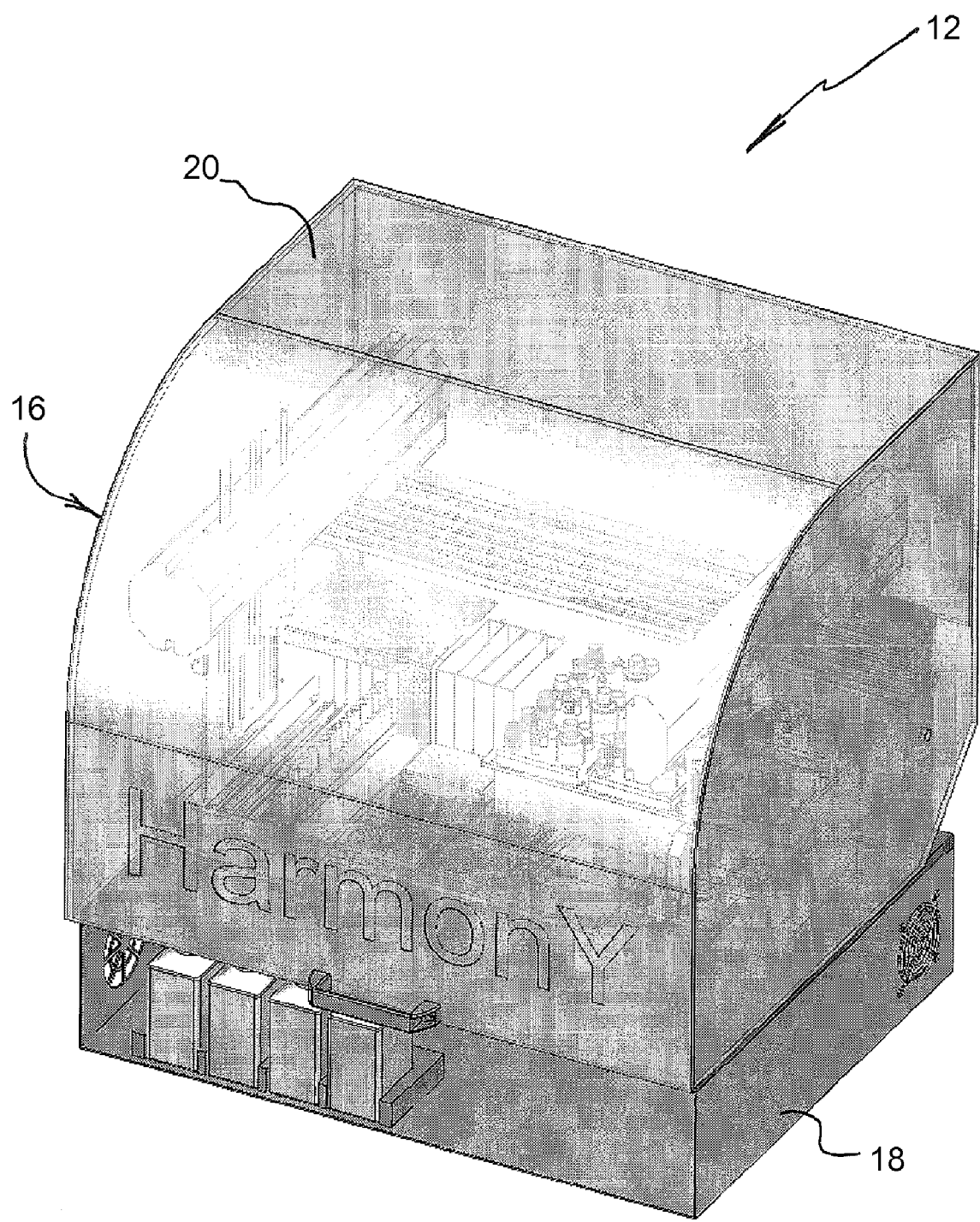
FIG. 1 is a front perspective view of a diagnostic workstation according to the present invention.
Figure 2:
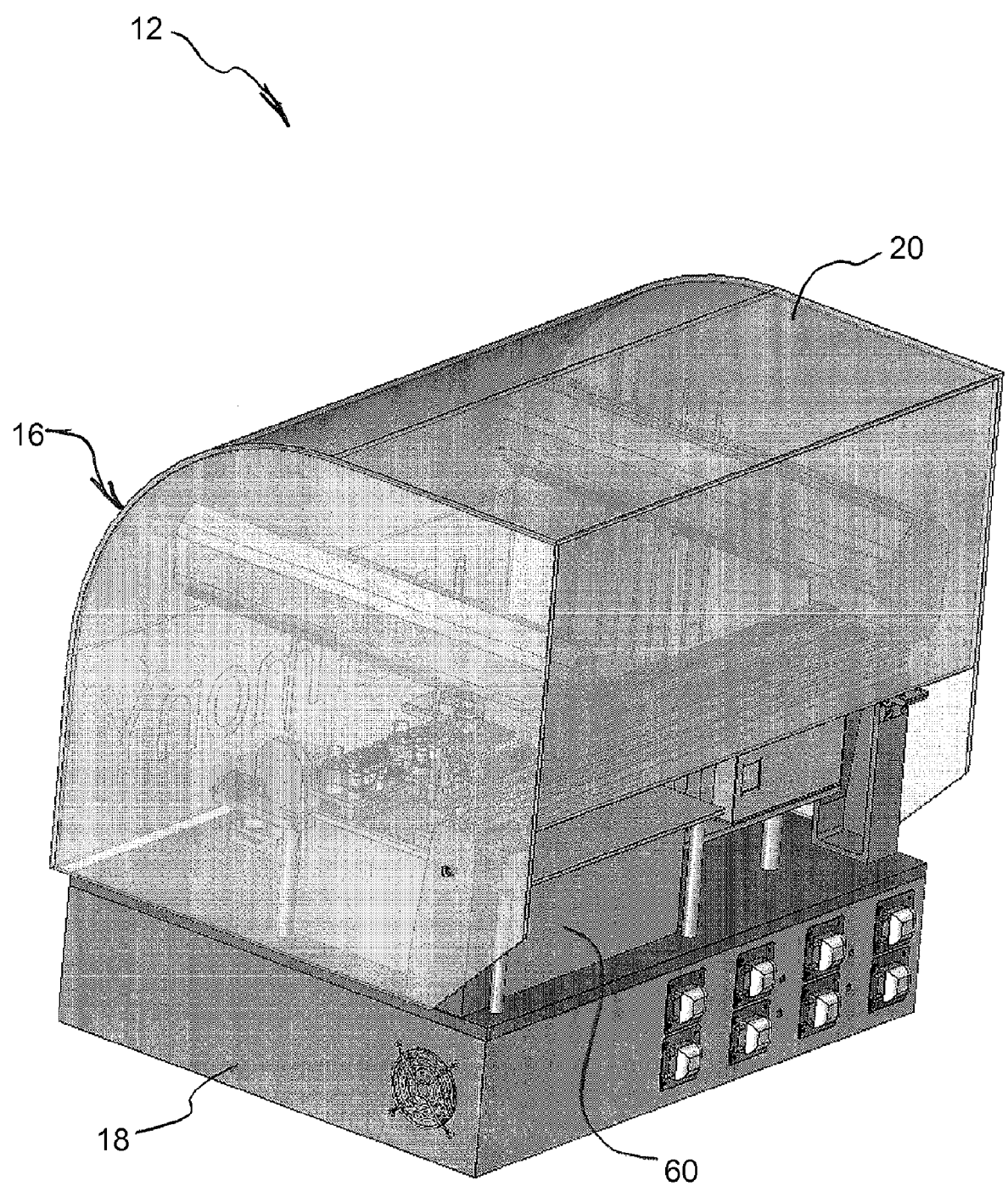
FIG. 2 is a rear perspective view of the diagnostic workstation shown in FIG. 1.
Figure 3:
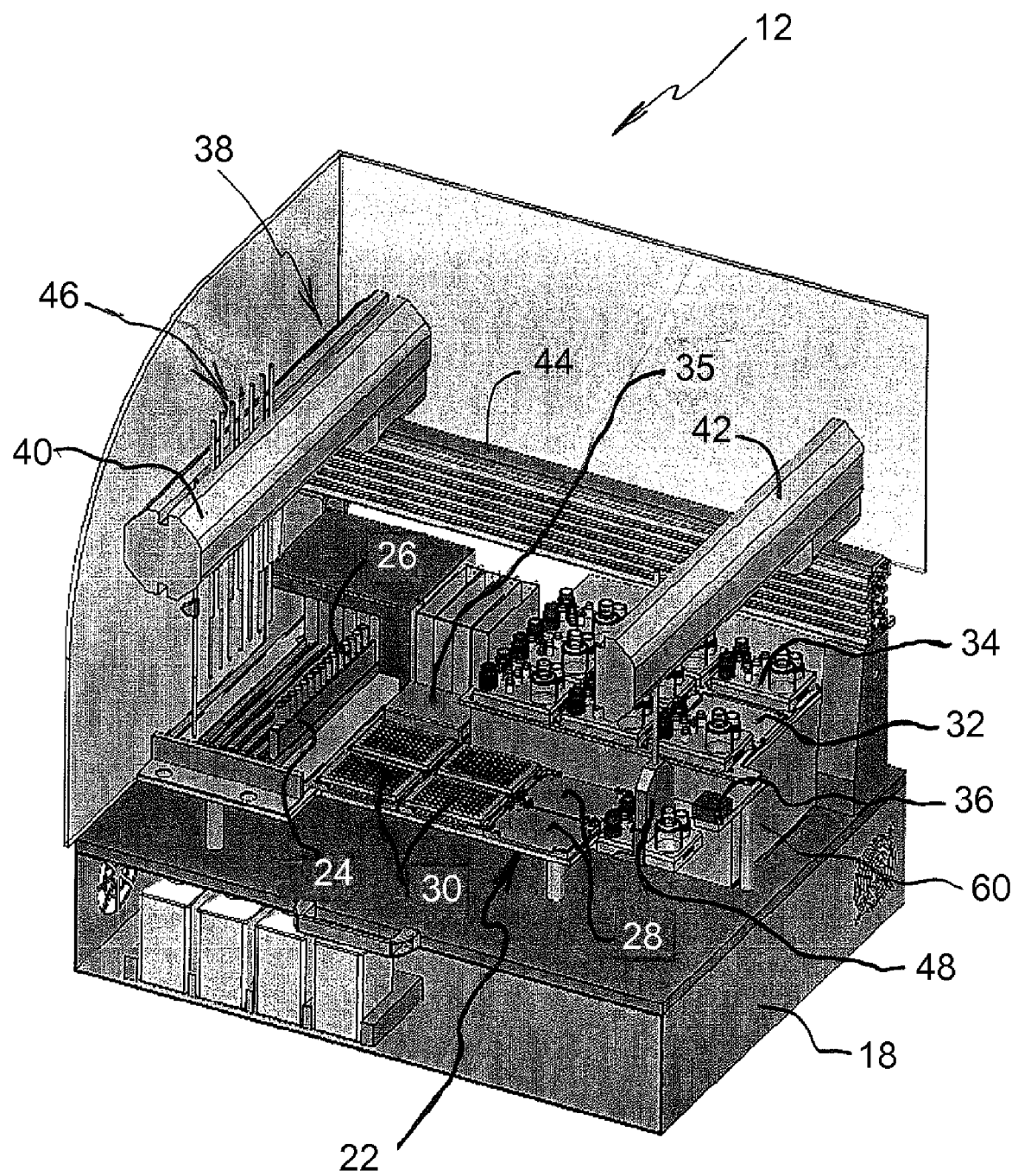
FIG. 3 is a front perspective view of the diagnostic workstation with a hood of the workstation partially removed to better show internal structure of the diagnostic workstation.
Figure 4:
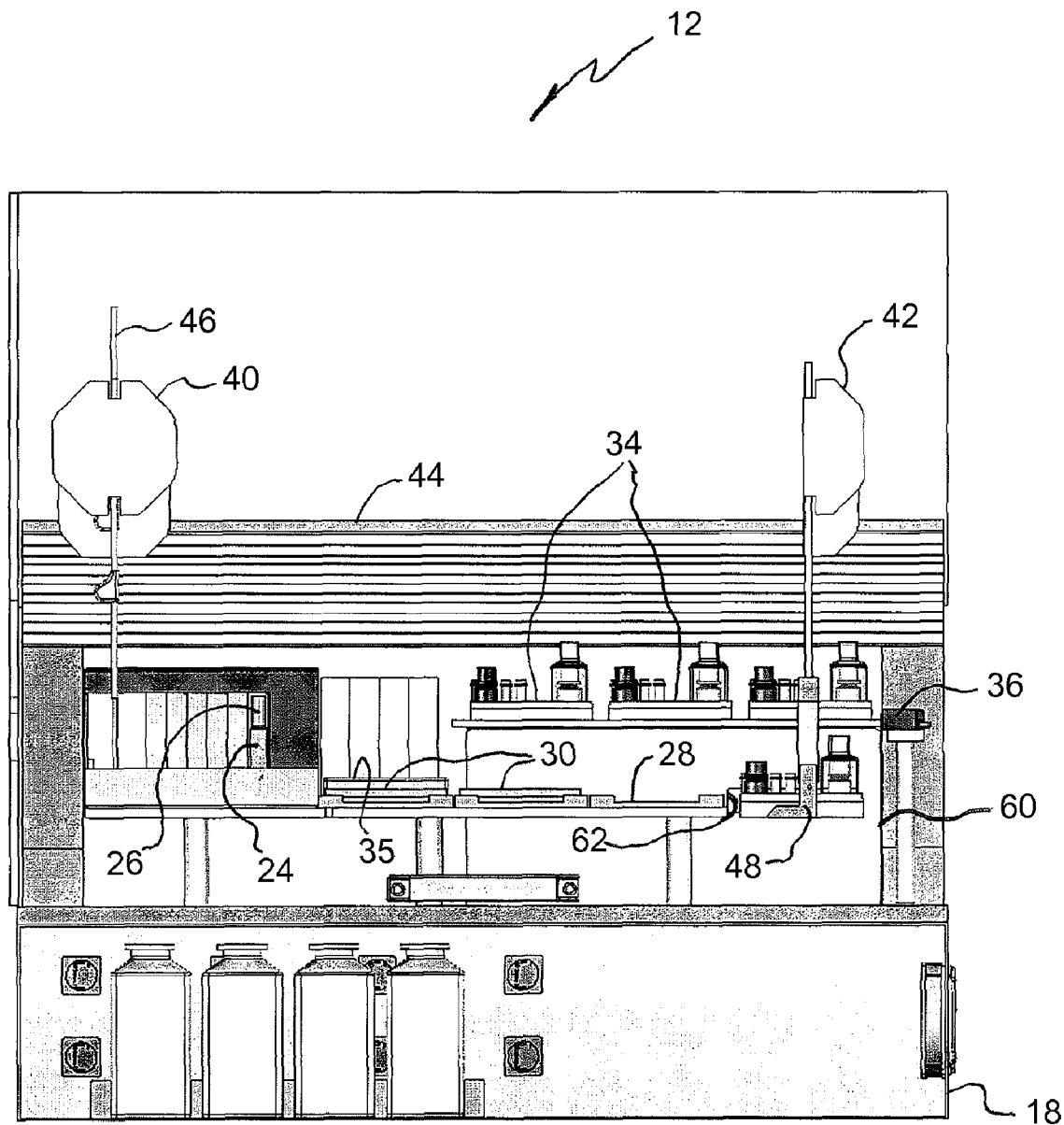
FIG. 4 is a front elevational view of the diagnostic workstation shown in FIG. 3.
Figure 5:
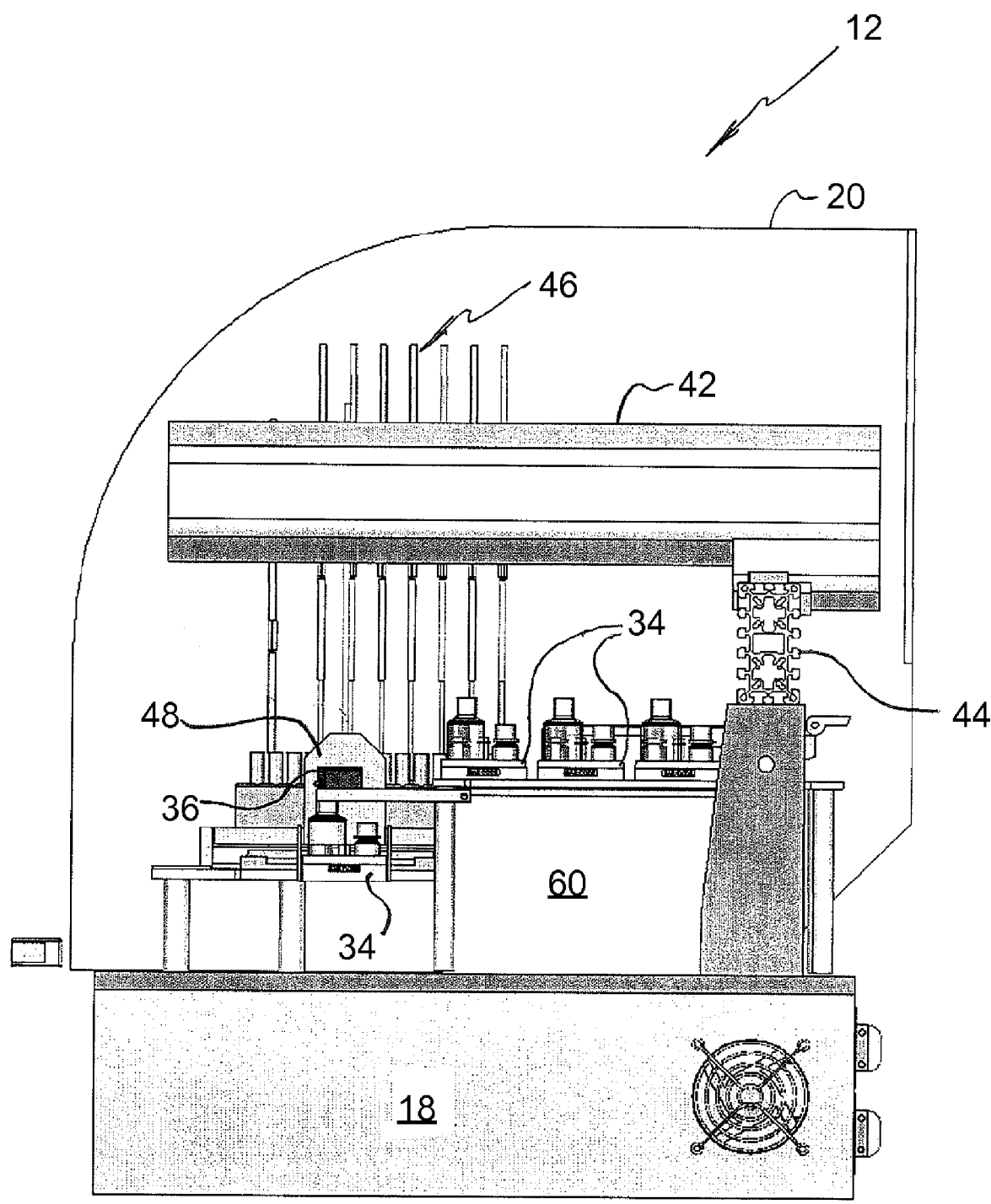
FIG. 5 is a side elevational view of the diagnostic workstation shown in FIG. 3.
Figure 6:
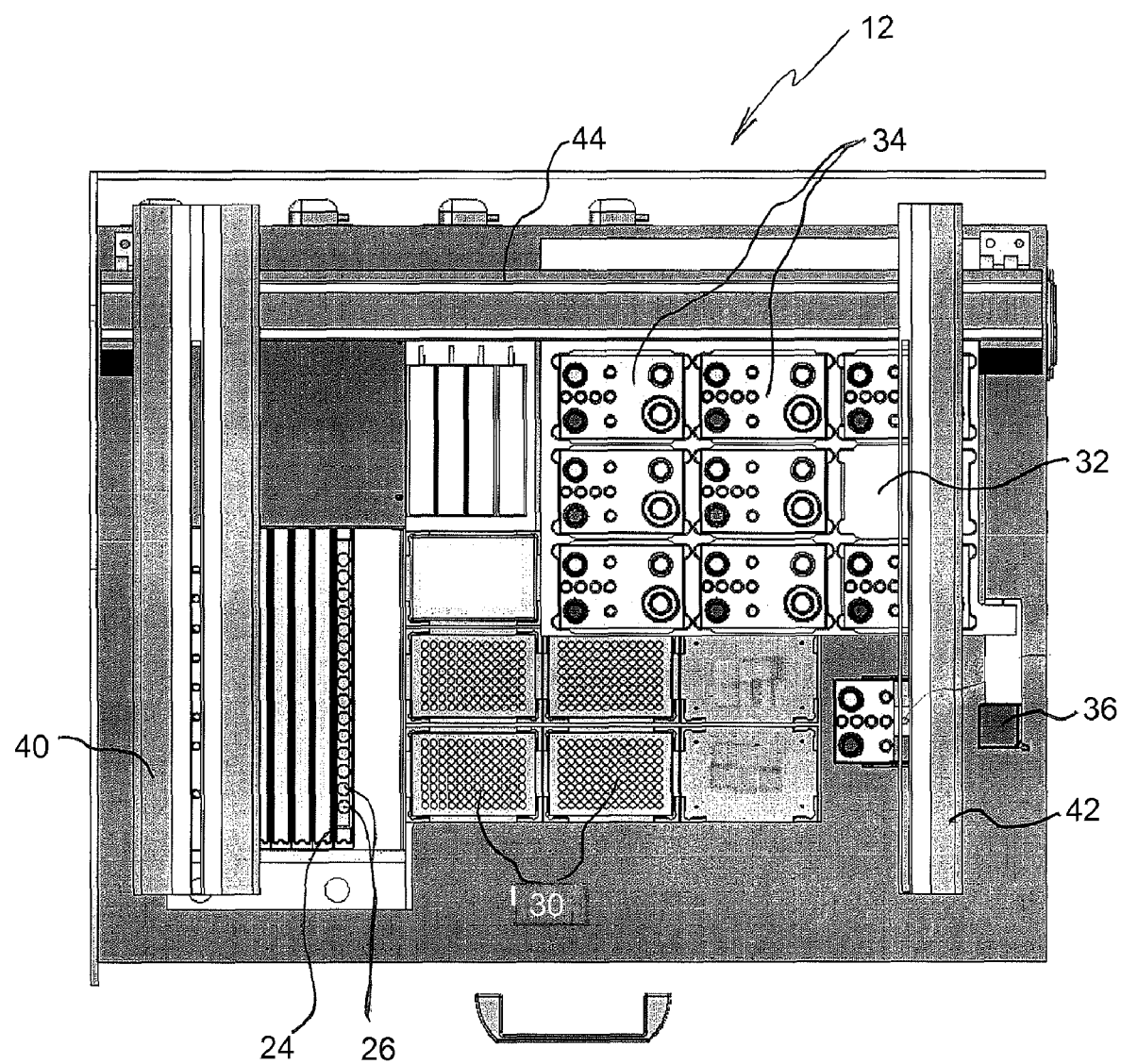
FIG. 6 is a top plan view of the diagnostic workstation shown in FIG. 5.

As used herein, the term "multiplex" in the context of an immunoassay should be understood to include a microarray assay, a magnetic bar-coded particle assay, or both, unless otherwise stated.

Reference is made initially to FIG. 1-6, which depict a diagnostic workstation 12 embodying the present invention. Diagnostic workstation 12 is capable of processing both standard singleplex and/or multiplex (magnetic particle based or planar microarray) ELISA or cell based functional assay sample wells. Diagnostic workstation 12 provides automated handling of ELISA well plates, samples, and reagents, and performs scheduled processing of indicated assays under either standard, microarray, or magnetic bar-coded particle test formats as indicated.

Workstation 12 comprises a housing 16 including a base 18. Housing 16 may further comprise a transparent hood 20 hinged to base 18. Workstation 12 further comprises a sample rack 24 supported from the base 18. The sample rack 24 may be configured to hold at least one sample tube 26, which may contain a test sample. Workstation 12 further comprises a plate nest 28, supported from the base, for receiving at least one well plate 30. Workstation 12 further comprises a kit nest 32, supported from the base, for receiving at least one reagent kit holder 34. The reagent kit holder 34 may carry reagents used to perform various types of assays.

Figure 8:
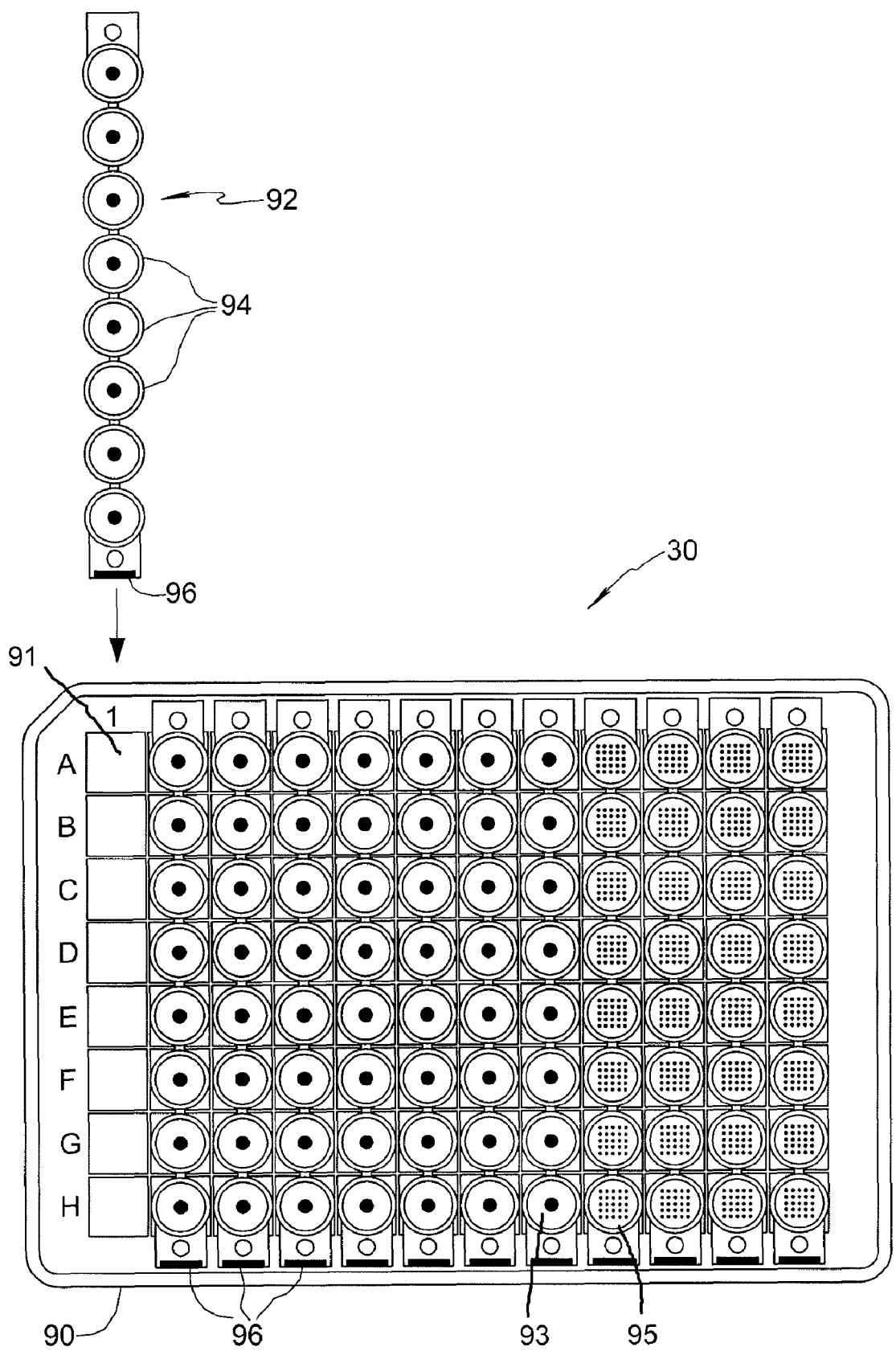
FIG. 8 is a top plan view of a configurable well plate having both standard and microarray wells in accordance with the present invention.

FIG. 8 depicts a well plate 30 which may be used with workstation 12. Well plate 30 comprises a plurality of strips nests 32 configured to hold linear well strips 92 each containing microwells 94. Each well strip 92 includes a uniquely identifiable machine-readable label 96 at one end thereof for indicating the type of test configuration (standard or multiplex) applied to the microwells 94 of the particular well strip 92. The label 96 may additionally indicate the particular ELISA protocol associated with the microwells 94 of the particular well strip 92. The uniquely identifiable machine-readable label 96 may be a barcode, and may be a one- or two-dimensional barcode.

In accordance with the present invention, well plate 30 may include a first well strip 93 having microwells 94. The microwells 94 of the first well strip 93 may have either a standard or multiplex immuno-assay configuration. The well plate 30 may also have a second well strip 95 having microwells 94. The microwells of the second well strip 95 may have an assay configuration different from the first well strip 93. Workstation 12 may be equipped to simultaneously accommodate various commercially available well plates, including but not limited to, microtiter plates, stripwell plates, and deepwell plates. When using barcodes, application of labels 96 on each well strip 92 may be achieved by reverse printing onto an underside of a transparent tab 91 of the well strip 92, or by other printing technique known in the art. It is desirable to provide a high quality and durable barcode marking at a readable location within available space constraints.

Workstation 12 further comprises an image detector 60, supported from the base 18, that may be used to read machine-readable labels 96 on well strips 92. The image detector 60 may be transportable and dockable. Image detector 60 may be a CCD camera or other two-dimensional opto-electronic imaging device sized to capture an image of a well plate 30, and may advantageously be in wireless communication with a computer system using any suitable wireless communication protocol, for example Bluetooth. Wireless communication is preferred because it enables image detector 60 to be transported within enclosure 16 in order to read labels 96 on well strips 92, without dragging wires through the interior of the housing 16.

Image detector 60 may be a multifunctional detection unit capable of absorbance detection, colorimetric detection, fluorescence excitation/detection, luminescence, chemi-luminiscence detection, and/or visible light detection. Image detector 60 may include a plurality of different readers providing different reading functions, or a single multifunctional reader. For absorbance detection, scanning wavelengths of 405 nm, 450 nm, or dual wavelength at 600-650 nm may be desirable. For colorimetric detection and fluorescence excitation/detection, a mega pixel range CCD imager and an excitation source such as a laser or multiple LEDs (light emitting diodes) capable of various excitation wave lengths and white light may be used. The optics of the reader may provide that fluorescent, chemi-luminescent (no excitation, but only emission detection) and transmitted light images can be recorded by the CCD in high resolutions (up to 10 micro meters/pixel or better). Image detector 60 may secure a received well plate 30 prior to read execution, and the excitation source (if any) intensity may be adjustable based upon the type of assay being performed. As may be understood, a control program may command image detector 60 to activate the relevant detection system and perform the required reading based on the type of test (standard, microarray, or magnetic bar-coded particle) and the particular test protocol. Image detector 60 may incorporate commercially available ELISA readers, for example, but not limited to, a Sensovation FLAIRplus technology.

Image detector 60 may, in the case of bar-coded particle assays, detect more than one instance of the target microwell(s). As a non-limiting example, the image detector 60 may use transmissive visible light imaging to capture an image of the barcodes of the particles, followed by fluorescence excitation/detection to capture an image of an assay result of the particles. Other combinations should be readily apparent to those having knowledge in the subject area.

Workstation 12 may comprise a second, less sophisticated image detector 35, for reading label 96 of well strips 92 and/or label 86 of reagent kit holders 34.

Workstation 12 may further comprise a reader 36, supported from the base 18, that may be used to read a uniquely identifiable machine-readable label 86 (FIG. 8) on each reagent kit holder 34. Reader 36 may be a barcode reader, and label 86 may be a barcode label. Image detector 60 and reader 36 may be capable of reading one-dimensional and two-dimensional barcodes. It is contemplated to locate label 96 on holder well strips 92 so that the label 96 may be read by reader 36 instead of image detector 60.

Workstation 12 further comprises a liquid handling system for performing pre-analytical steps generally designated as 38. Liquid handling system 38 is shown as including a movable arm 40, supported from the base 18, which may be a gantry arm. FIGS. 1-6 depict a workstation 12 having two movable arms 40, 42 extending in a front-to-rear direction above base 18 and a rail 44 extending in a transverse direction above a rear portion of deck area 22. It should be recognized that a workstation of the present invention may have as few as one movable arm. Movable arms 40, 42 are mounted at their rear ends to rail 44 for automated transverse motion along rail 44. Movable arms 40, 42 may be equipped with a pipetting tool 46 for withdrawing sample fluid from a sample tube 26 or reagents from a reagent kit holder 34 and delivering the withdrawn fluid to microwells 94 of well plates 30. Liquid handling system 38 may further include a gripper tool 48 depending from movable arm 42 for lifting and transporting a selected well plate 30 or a selected reagent kit holder 34. As may be understood, pipetting tool 46 and gripper tool 48 may be supported from the same movable arm, when a workstation comprises a single movable arm. Liquid handling system 38 may be configured using a commercially available liquid handling system and accessories.

By way of non-limiting example, the BIOMEK® 3000 laboratory automation workstation available from Beckman Coulter, Inc. provides a suitable liquid handling system which may be adapted for use in practicing the present invention. A second example may be DYNEX's DSX 4 plate model which is also adaptable for this need.

Workstation 12 further comprises a controller in communication with the movable arm 40, pipetting tool 46, and image detector 60. The controller may further be in communication with other components of the workstation 12, if present, including, but not limited to, the reader 36, the image detector 35, and/or the gripper tool 48. The controller may receive data and send control signals to the various components of the workstation to automatically perform assays. The controller may be a computer running a control program. Workstation 12 may further comprise an input device, in communication with the controller, for receiving input from an operator. Workstation 12 may further comprise a display in communication with the controller.

Figure 7:
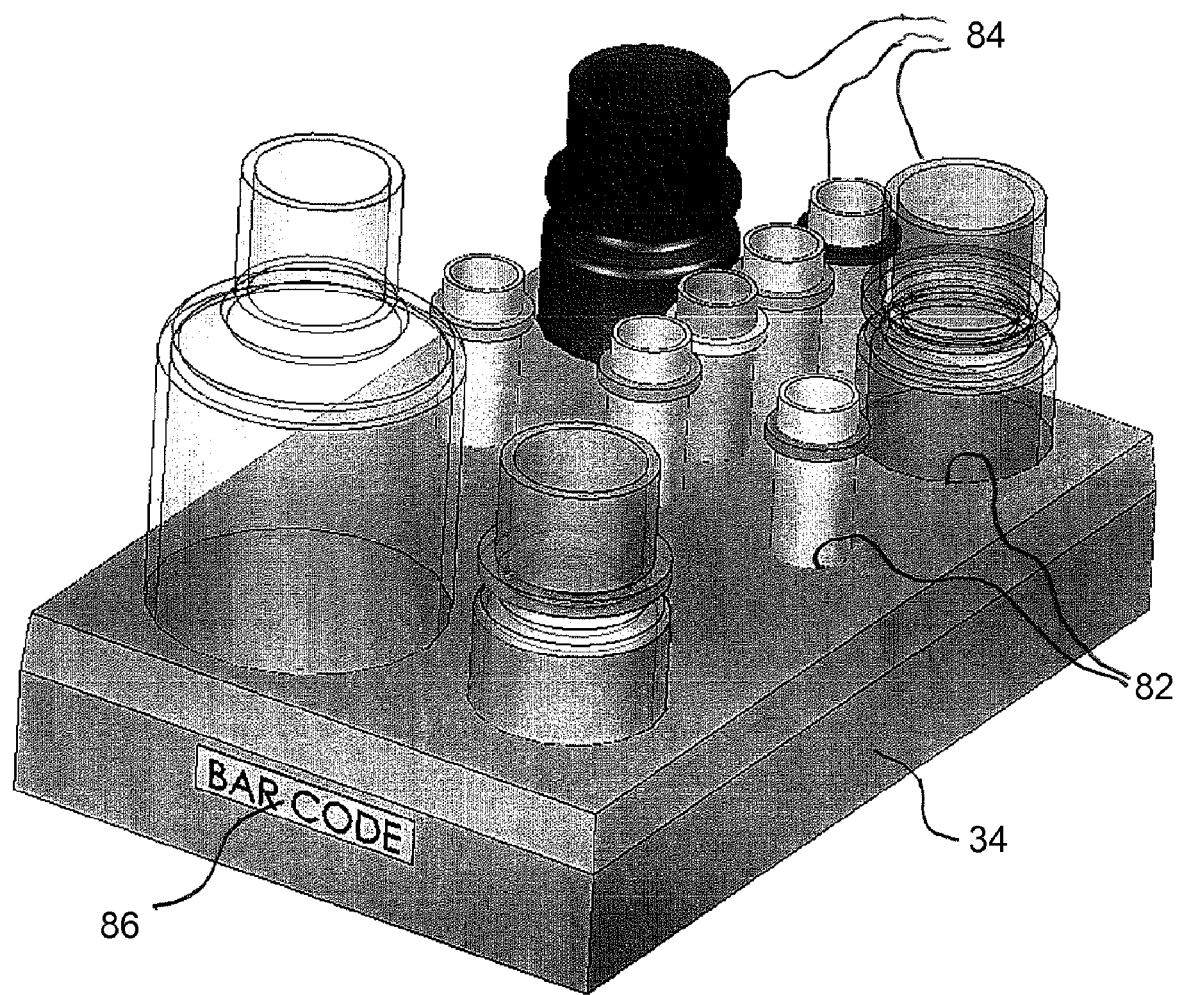
FIG. 7 is a perspective view of a reagent kit holder used in connection with the diagnostic workstation.

FIG. 7 shows a reagent kit holder 34 in greater detail. Reagent kit holder 34 may have a plurality of recesses 82 therein and a plurality of reagent bottles 84 received in recesses 82. Each kit holder 34 may have enough recesses 82 of proper size to accommodate the maximum number of reagent bottles found in a commercially available reagent kit. Reagent bottles 84 in holder 34 may be allocated to recess 82 in a predetermined arrangement known to the control program to enable mapping of the reagent bottles 84. Each reagent kit holder 34 is provided with a uniquely identifiable machine-readable label 86 uniquely identifying the reagent kit holder 34. Label 86 may be correlated to a scanned UPC code from a reagent kit box, such that information about the commercial kit stored in a database or look-up table is assignable to a particular reagent kit holder 34 in which the reagent bottles from the kit are carried. Accordingly, label 86 on reagent kit holder 34 indicates to a control program the type of assay for which the carried reagent bottles 84 are intended and the location of each reagent in the reagent kit holder 34. The UPC code on the kit box may be scanned using reader 36, which may be a barcode reader. Label 86 may be read by reader 36 either by manually scanning the label 86 as the reagent kit holder 34 is loaded into the workstation 12, or automatically by operating gripper tool 48 to retrieve a reagent kit holder 34 in the kit nest 32, move it near reader 36 for a scan, and return the reagent kit holder 34 to its assigned nest. It is also contemplated to locate label 86 on reagent kit holder 34 so that label 86 may be read by image detector 60 instead of reader 36

Workstation 12 may further comprise a magnet or a magnetized component (such as plate nest 28) to aid in anchoring magnetic bar-coded particles to the inside of the bottom of the microwells, when such assays are performed. Alternatively, well plate 30 may include a magnet. Magnetic attraction may be used throughout the workstation 12 where the contents of the microwells 92 need to be restrained (stages during reagent addition, washes and reading).

Figure 9:
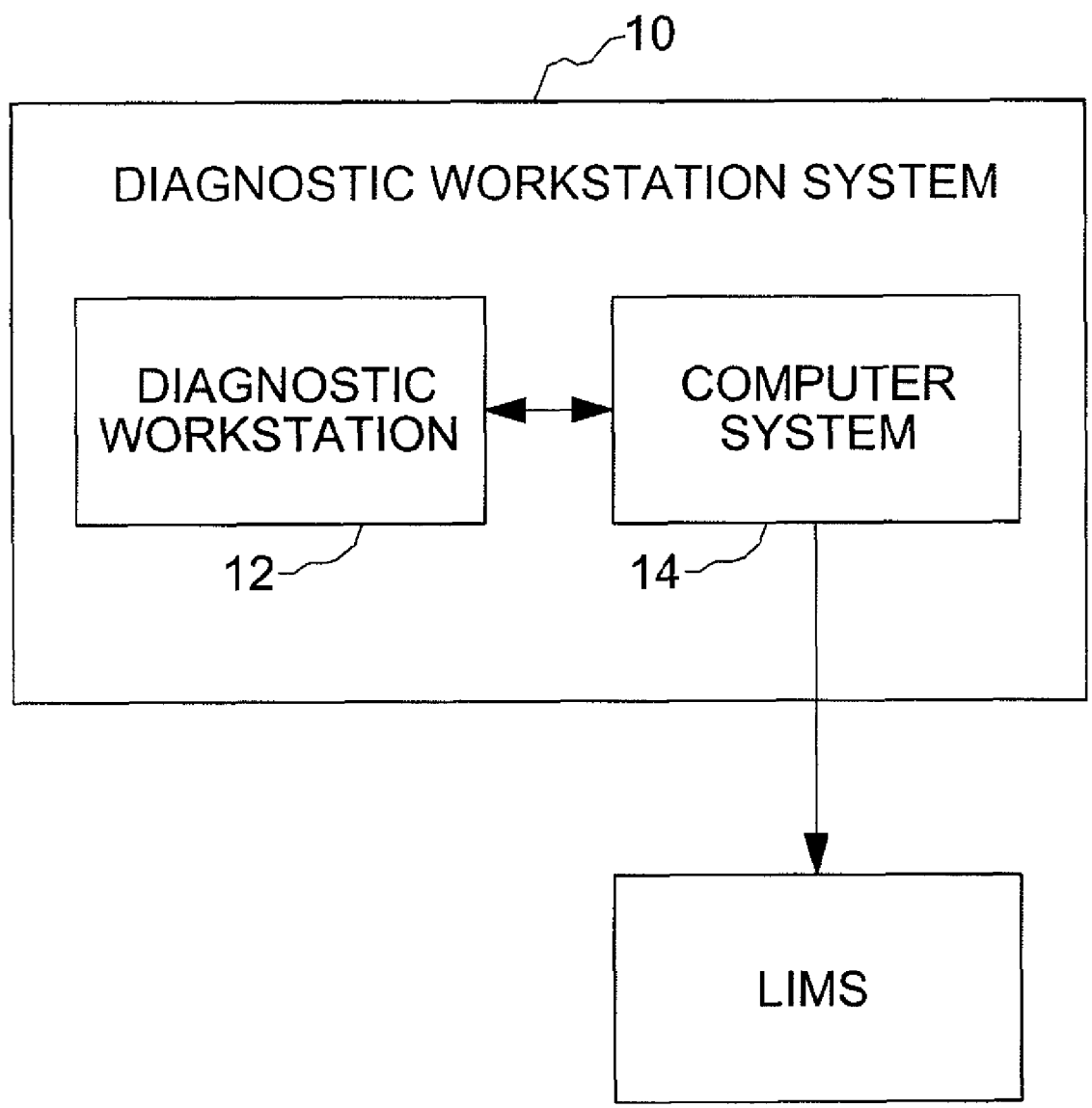
FIG. 9 is a schematic block diagram of a diagnostic system including a workstation of the present invention.

FIG. 9 depicts that a diagnostic system 10 wherein a diagnostic workstation 12 may communicate measurement results to a computer system 14, which in turn may be linked to a Laboratory Information Management System ("LIMS") such that measurement results may be uploaded to the LIMS.

Reference is now made to FIGS. 10-16 for operational description of diagnostic workstation 12, and methods for performing assays using the workstation.

Figure 10:
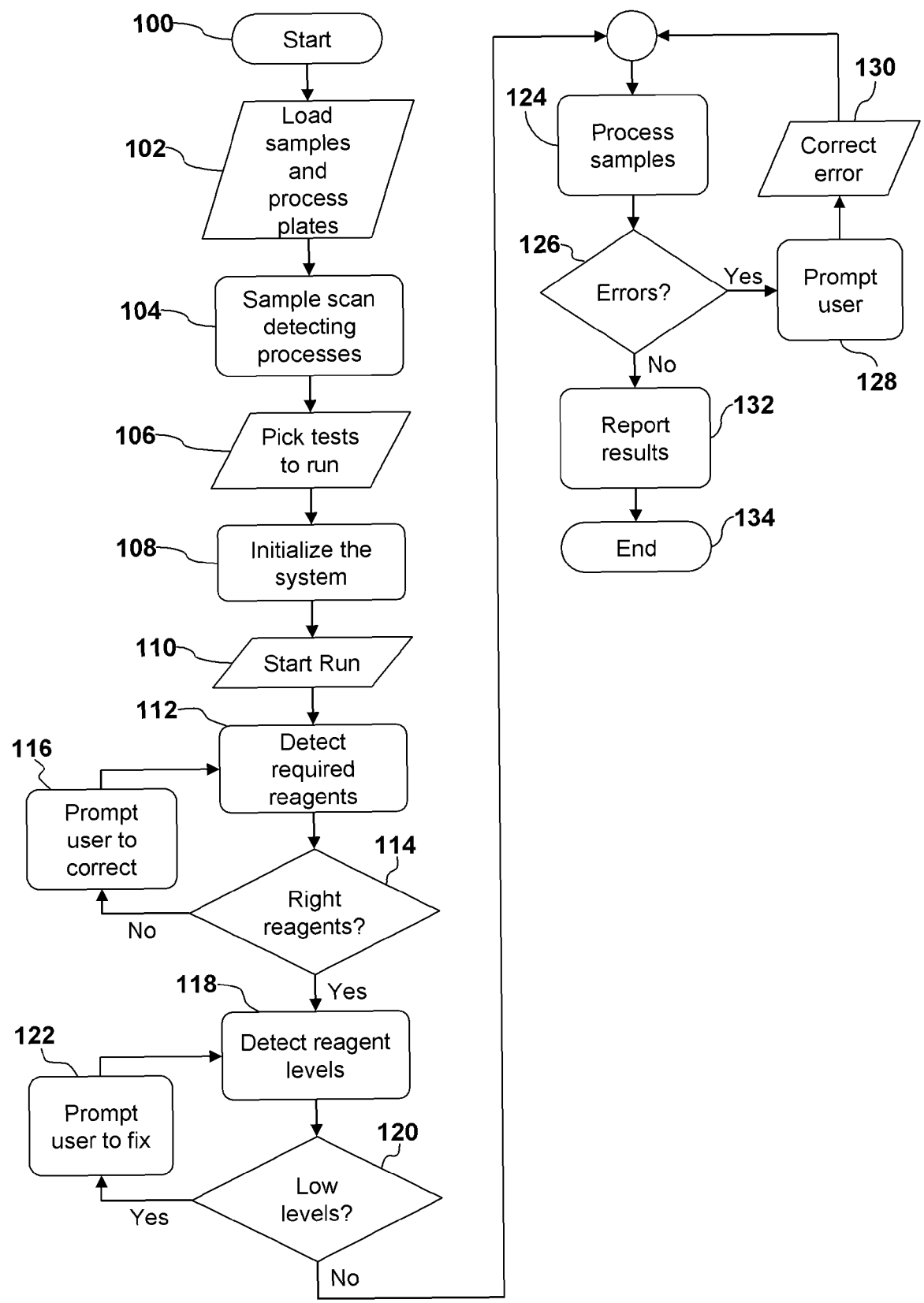
FIG. 10 is a process workflow diagram describing operation of the diagnostic workstation.

FIG. 10 provides an overall process workflow diagram. Flow starts at 100. First, sample tubes 26 and process plates (including well plates 30 and reagent kit holders 34) are loaded by a user into workstation 12 in accordance with step 102, with kit box UPC codes and labels 86 on reagent kit holders 34 being scanned and read as the kit holders are loaded. In step 104, a sample scan is conducted to read label information on loaded samples and on loaded well plates 30. As described above, a given well plate 30 may include one or more well strips 92 having microwells 94 configured for standard ELISA, and one or more well strips 92 having microwells 94 configured for multiplex ELISA, and the label 96 associated with a given well strip 92 identifies the type of test format (standard or multiplex) and the particular intended ELISA protocols that may be executed. A list of available tests that may be performed based on the readings of the respective sample tubes, well plates 30, and reagent kit holds 34 is retrieved. A menu of the available tests is displayed on a display, and an operator may provide an input to select the test(s) to run to establish a process matrix in accordance with step 106. In step 108, the workstation is initialized, and in step 110 the operator may enter a command to start execution of the tests. During execution, the required reagents must be detected pursuant to step 112; if not, query 114 causes the operator to be prompted in step 116 to correct the reagent error. Once the correct reagents are confirmed by query 114, reagent levels are detected pursuant to step 118. If reagent levels are low according to query 120, then the operator is prompted in step 122 to take corrective action. Once the reagent levels are confirmed by query 120, the samples are processed as indicated by step 124. If errors are detected during processing, query 126 branches flow to prompt the user in step 128 and the user may correct the error in step 130. If no errors are present, query 126 allows flow to continue to step 132 wherein measurement results are reported. Flow ends at 134.

Figure 11:
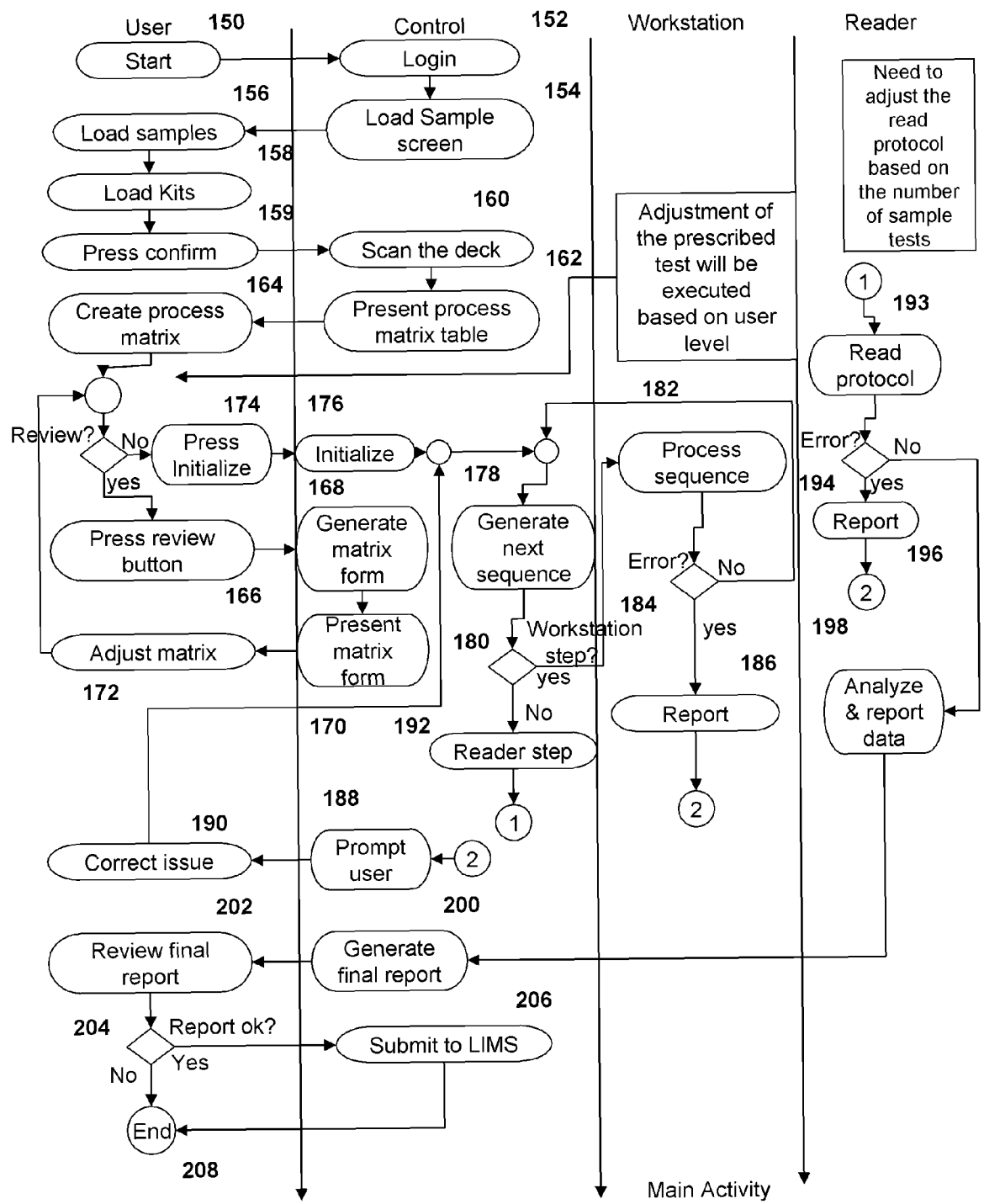
FIG. 11 is a main activity flow diagram of the diagnostic workstation.
Figure 12:
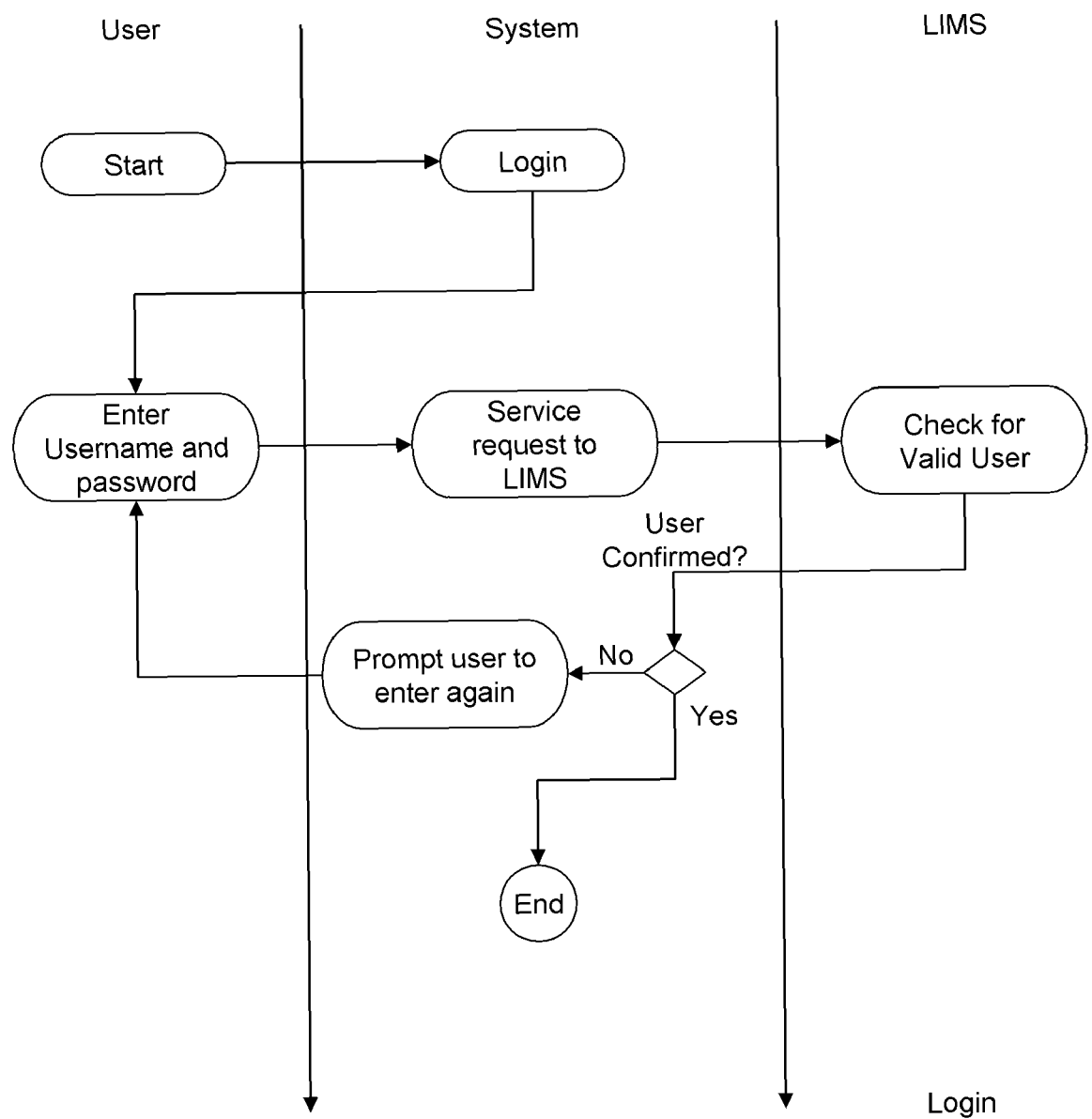
FIG. 12 is a login activity flow diagram of the diagnostic workstation.
Figure 13:
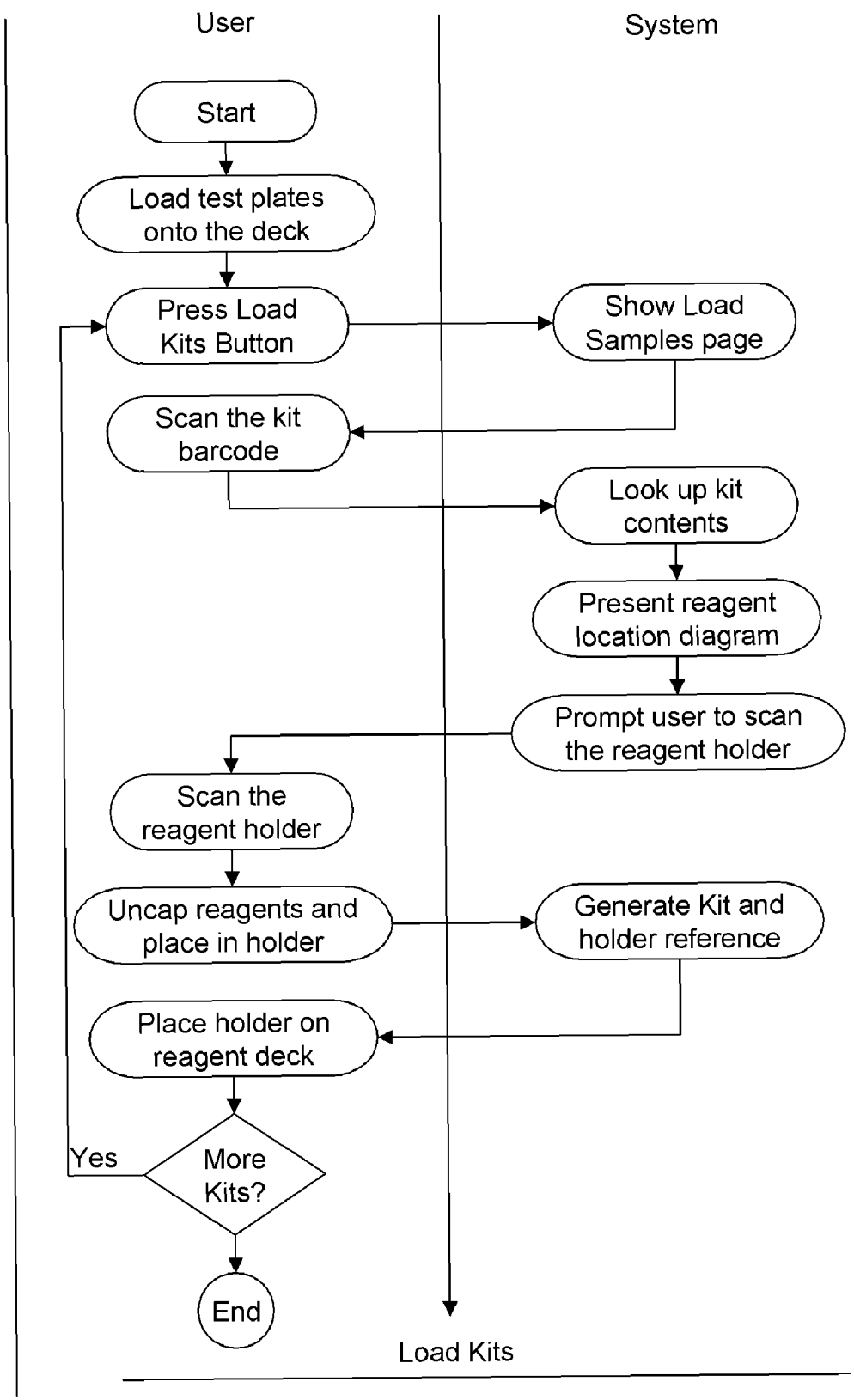
FIG. 13 is kit load activity flow diagram of the diagnostic workstation.
Figure 14:
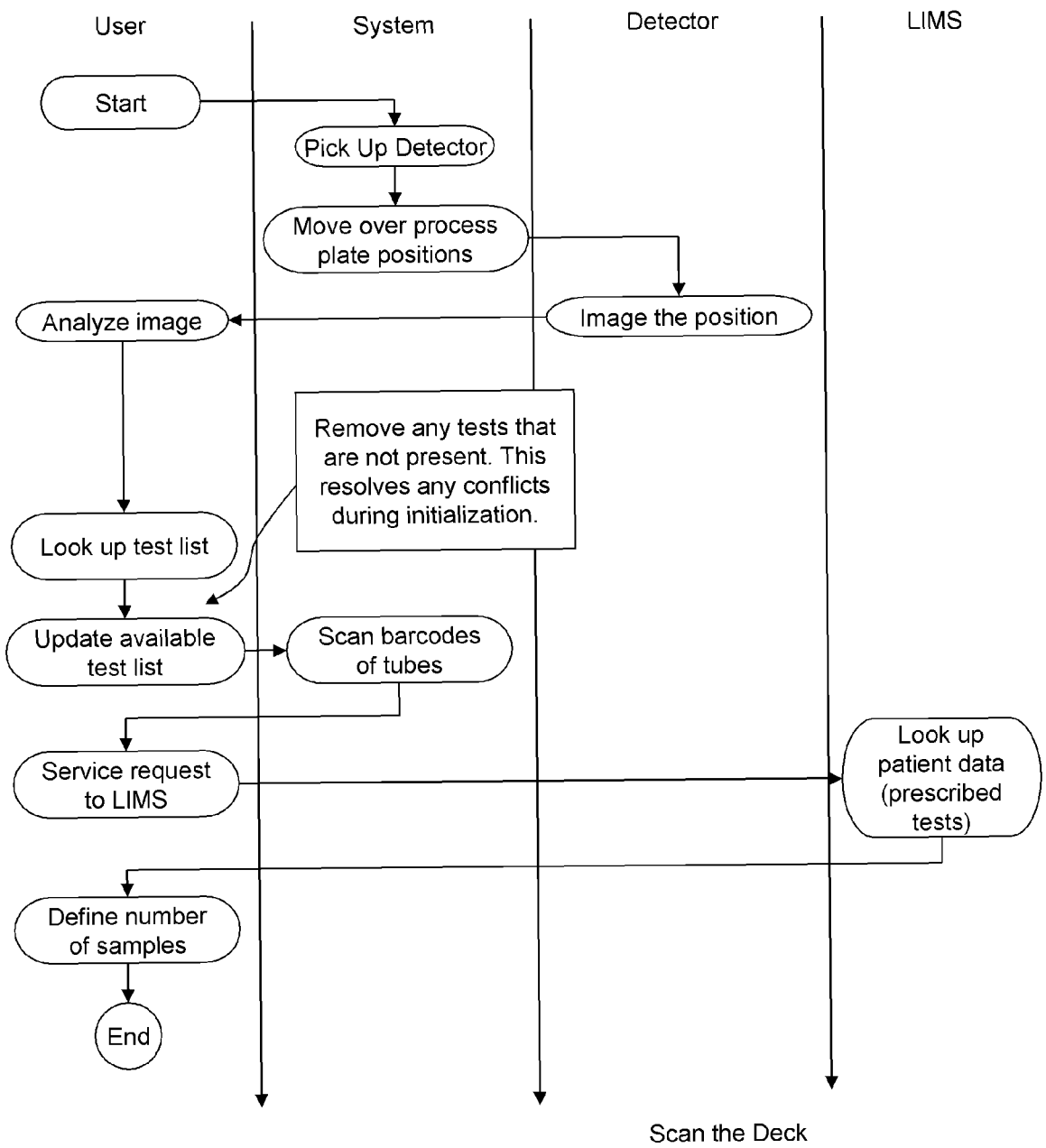
FIG. 14 is a deck scan activity flow diagram of the diagnostic workstation.
Figure 15:
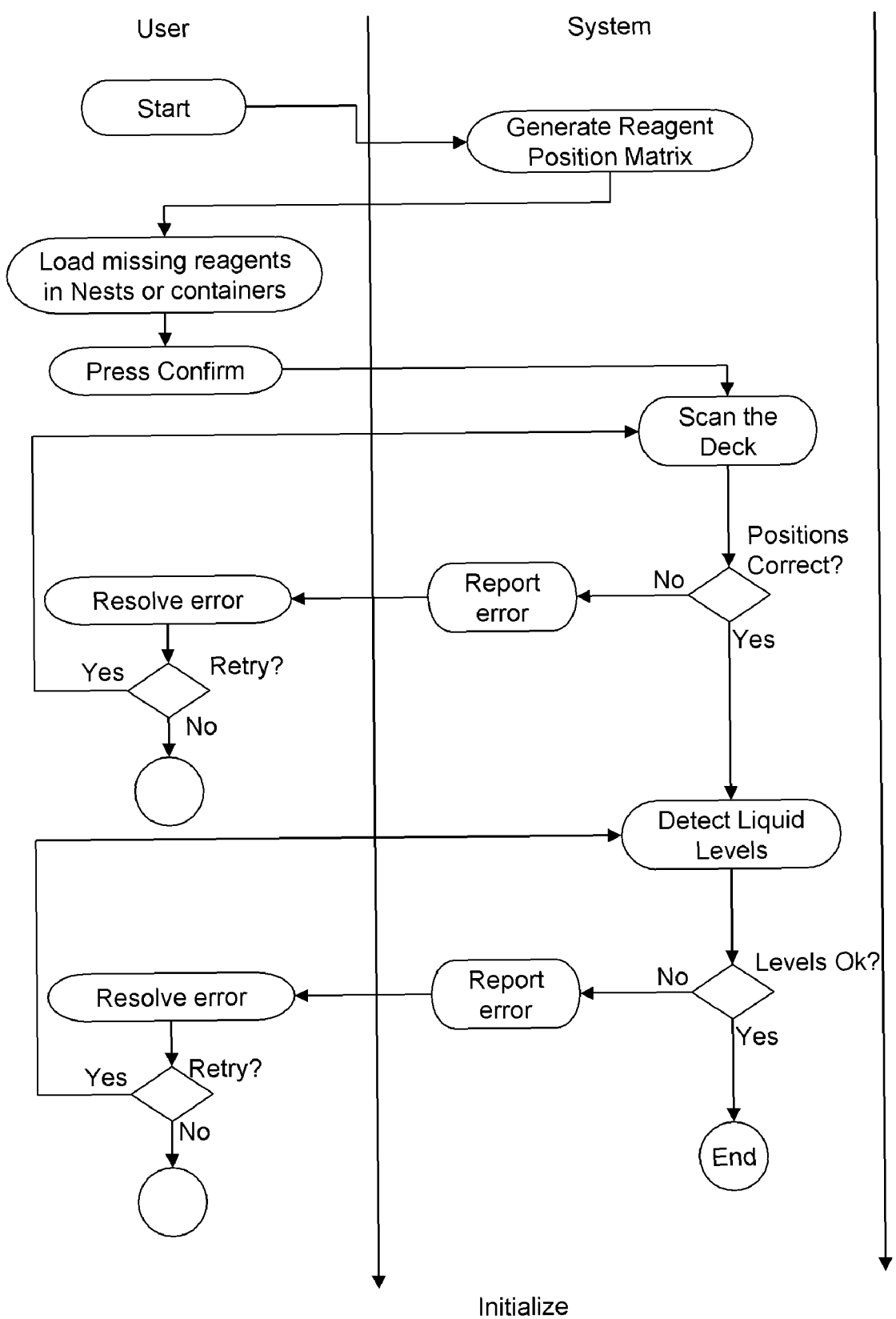
FIG. 15 is an initialization activity flow diagram of the diagnostic workstation.
Figure 16:
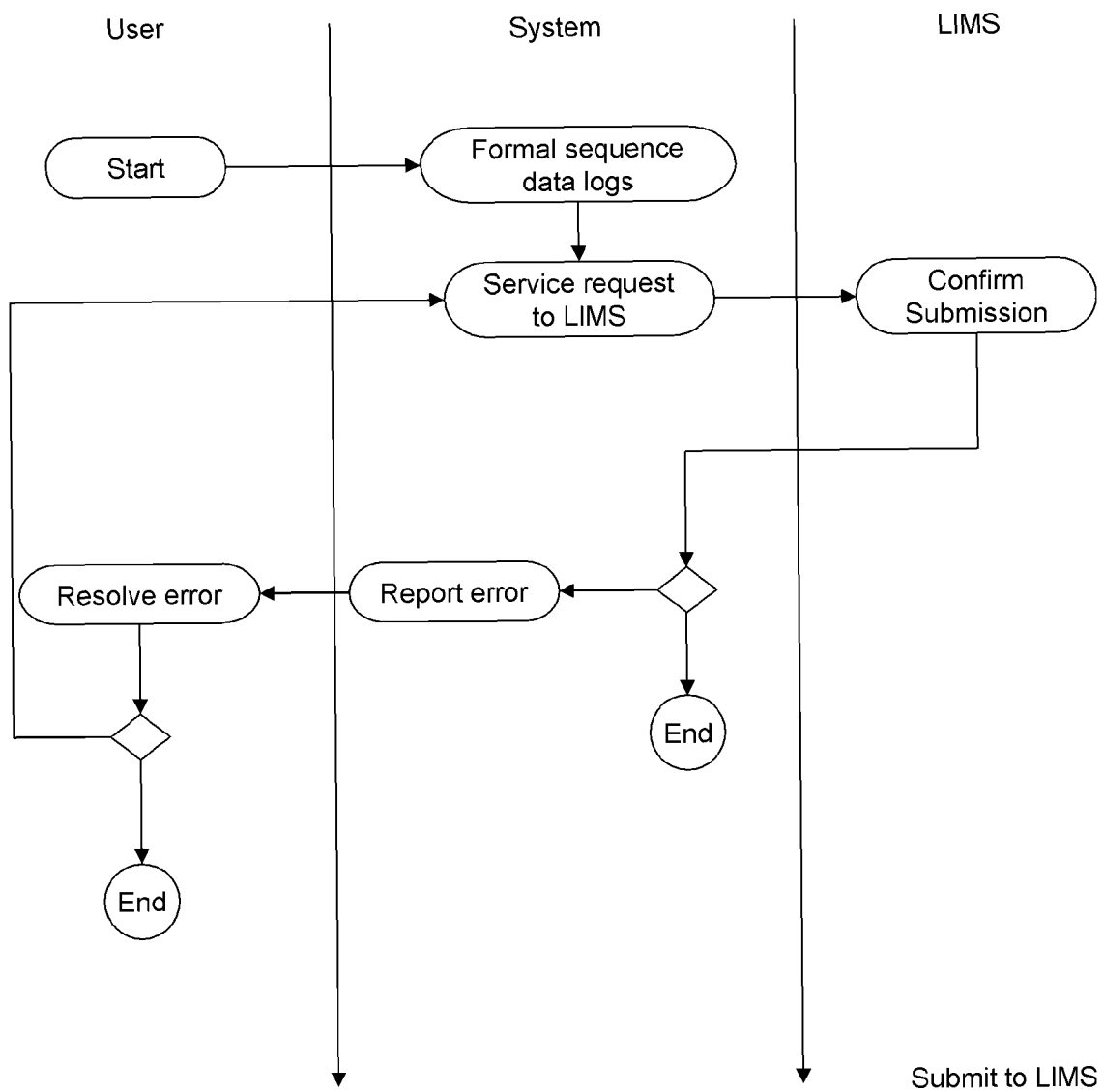
FIG. 16 is a submit-to-LIMS activity diagram of the diagnostic workstation.

The main activity flow diagram of FIG. 11 provides further detail in association with various routine flow diagrams presented in FIGS. 12-16. Flow starts at 150. A login routine 152 (see FIG. 12) is executed by the control software and then a Load Sample screen is displayed in step 154. The operator then loads the samples tubes 26 into sample rack 24 and the well plates 30 into well plate nest 28 in accordance with step 156. A load kit routine 158 (see FIG. 13) is then executed to cause the operator to populate reagent kit holders 34 and load the reagent kit holders into kit nests 32. As may be understood, from FIG. 13, the operator may scan the UPC barcode on the kit box to enable retrieval of stored information about the kit contents and a reagent location diagram or map, and then the operator may scan the reagent holder 34, uncap reagent bottles 84 and place them in recesses 82, and place the reagent kit holder 34 in kit nest 32. The operator then presses <CONFIRM> to initiate a scanning routine 160 (see FIG. 14) to read in label information from well plates 30 and sample tubes 26 and retrieve patient data from the LIMS.

The acquired information from the scan is processed and a process matrix table listing available tests, based on the reagent kits holder(s) 34 loaded into the workstation 12, is presented in step 162 in a manner allowing the operator to assign specific assays to particular sample microwells. In step 164, the operator assigns specific assays to run for each of the samples to create a process matrix, which the operator may choose to review by pressing <REVIEW> in step 166. For review purposes, a matrix form is generated in step 168 and presented in step 170, and the operator may make adjustments to the process matrix in step 172. Once the process matrix is in final form, the operator may press <INITIALIZE> according to step 174 to execute an initialization routine 176 (see FIG. 15). As will be appreciated, the process matrix for a given well plate may include well strips having standard format microwells and well strips having multiplex format microwells (either microarray or magnetic bar-coded particle).

After the workstation is initialized, flow continues at step 178 wherein the control program determines the next sequence step to be carried out based on the process matrix (step 178 may be initiated by the operator pressing <START RUN>, however this step is not depicted). Query 180 determines if the next sequence step is a "workstation" step involving liquid handling, incubation, washing, etc., as opposed to a final "reader" step in which results are obtained through imaging. If the next step is a workstation step, flow continues at step 182 and the sequence step is executed. If an error results as determined by query 184, then flow is directed to step 186 and the error is reported by the workstation. The control program then prompts the operator in step 188 and the operator corrects the error in step 190 before flow resumes at step 178 and the next sequence step is determined.

If query 180 indicates that the next sequence step is a "reader" step, then the reader unit 60 is activated and a read protocol is executed according to step 192. If a read error is detected at query 194, the error is reported by the reader in step 196 and flow is directed to step 188 mentioned above. If the read protocol is successful, then the image data is analyzed and reported to the control program in step 198. The control program generates a final report in step 200 which may be reviewed by the user in step 202. If the report is acceptable pursuant to query 204, then the test results are submitted to the LIMS in accordance with routine 206 (see FIG. 16).

While a preferred form of this invention has been described above and shown in the accompanying drawings, it should be understood that applicants do not intend to be limited to the particular details described above and illustrated in the accompanying drawings. Thus, it is the desire of the inventors of the present invention that it be clearly understood that the embodiments of the invention, while preferred, can be readily changed and altered by one skilled in the art and that these embodiments are not to be limiting or constraining on the form or benefits of the invention.

What is claimed is:

1. An automatic diagnostic workstation, comprising:
a housing having a base;
a sample rack supported from the base, the sample rack being configured to receive at least one sample tube;
a plate nest supported from the base, the plate nest being configured to receive at least one well plate having at least one well strip;
a kit nest supported from the base, the kit nest being configured to receive at least one reagent kit holder;
a movable arm supported from the base;
a pipetting tool supported from the movable arm, for transferring one or more samples contained by the sample tube and/or one or more of the reagents of the reagent kit holder;
an image detector for reading a uniquely identifiable machine readable label of the well strip and for capturing an image of contents of one or more microwells of the well strip; and
a controller for automatically performing an assay on contents of the well strip, the controller communicating with the movable arm, the pipetting tool, and the image detector.

2. The workstation of claim 1, wherein the well plate is capable of holding a heterogeneous mix of well strips selected from singleplex well strips, microarray well strips, and/or magnetic bar-coded particle well strips, and the controller is capable of performing assays according to each type of well strip.

3. The workstation of claim 1, wherein the image detector detects a colorimetric signal, fluorescence signal, absorbance signal, luminescence signal, chemi-luminiscence signal and/or visible transmitted light signal.

4. The workstation of claim 3, wherein the image detector detects more than one of a colorimetric signal, fluorescence signal, absorbance signal, luminescence signal, chemi-luminiscence signal and/or visible transmitted light signal.

5. The workstation of claim 1, further comprising a reader for reading a uniquely identifiable machine-readable label of the reagent kit holder.

6. The workstation of claim 1, further comprising a magnet proximate to the plate nest for restraining magnetic bar-code beads of a magnetic bar-code bead well strip.

7. The workstation of claim 6, wherein the magnet is an electromagnet.

8. The workstation of claim 1, wherein the movable arm is a gantry arm.

9. The workstation of claim 1, further comprising a gripper tool for gripping well plates and/or reagent kit holders, the gripper tool being supported from the movable arm.

10. The workstation of claim 9, wherein the movable arm is capable of selectively activating either the pipette tool or the gripper tool.

11. The workstation of claim 1, wherein a uniquely identifiable machine-readable label of the reagent kit holder is a one-dimensional bar code or a two-dimensional barcode.

12. The workstation of claim 1, wherein the uniquely identifiable machine-readable label of the strip is a one-dimensional bar code or a two-dimensional barcode.

13. The workstation of claim 1, wherein the image detector is in communication with a computer system.

14. The workstation of claim 13, wherein the image detector is in wireless communication with the computer system.

15. A well plate for performing assays, comprising:
- a plurality of strip nests, each strip nest configured to hold a well strip;
- a first well strip held in a first strip nest, the first well strip having a plurality of microwells and a uniquely identifiable machine-readable label, and wherein all of the microwells of the first well strip contain an assay selected from the group consisting of a singleplex assay, a microarray assay, and a magnetic bar-coded particle assay;
- a second well strip held in a second strip nest, the second well strip having a plurality of microwells and a uniquely identifiable machine-readable label, and wherein the microwells of the second well strip contain an assay selected from the group consisting of a singleplex assay, a microarray assay, and a magnetic bar-coded particle assay; and
- wherein the assay contained in the microwells of the first well strip is different than the assay contained in the microwells of the second well strip.

16. The well plate of claim 15, wherein the uniquely identifiable machine-readable labels of the well strips identify the assay contained in the corresponding well strip.

17. The well plate of claim 15, further comprising a magnet arranged to attract a ferromagnetic object contained in the microwells to an inside bottom surface of the microwells.

18. A method for automatically performing assays, comprising the steps of:
- using a reader to read a uniquely identifiable machine-readable label of a reagent kit holder and a sample tube;
- using an image detector to read a uniquely identifiable machine-readable label of a well strip of a well plate;
- retrieving a list of available tests based on the readings of the respective labels of the sample tube, well strip, and reagent kit holder;
- displaying the list of available tests on a display;
- receiving an input from an operator selecting at least one of the displayed tests; and
- performing the selected test(s).

19. The method of claim 18, further comprising the steps of:
- detecting a level of a reagent in the reagent kit holder;
- determining if the level of the reagent is lower than a predetermined value; and
- prompting the operator to correct an error if the level is determined to be lower than the predetermined value.

20. The method of claim 18, further comprising the steps of:
- detecting a required reagent in the reagent kit holder;
- determining if the required reagent is not present; and
- prompting the operator to correct an error if the required reagent is not present.

21. The method of claim 18, further comprising the steps of:
- using the image detector to capture an image of a microwell of the well strip; and
- sending the captured image to a computer system.

* * * * *